(12) United States Patent
Nguyen et al.

(10) Patent No.: US 9,115,214 B2
(45) Date of Patent: Aug. 25, 2015

(54) METHODS FOR CONTROLLING PRETREATMENT OF BIOMASS

(71) Applicant: ABENGOA BIOENERGY NEW TECHNOLOGIES, LLC, Chesterfield, MO (US)

(72) Inventors: Quang A. Nguyen, Chesterfield, MO (US); Weidong He, Chesterfield, MO (US); Leroy D. Holmes, Florissant, MO (US)

(73) Assignee: Abengoa Bioenergy New Technologies, LLC, Chesterfield, MO (US)

( * ) Notice: Subject to any disclaimer, the term of this patent is extended or adjusted under 35 U.S.C. 154(b) by 543 days.

(21) Appl. No.: 13/625,525

(22) Filed: Sep. 24, 2012

(65) Prior Publication Data

US 2014/0083939 A1    Mar. 27, 2014

(51) Int. Cl.
| | | |
|---|---|---|
| *C12M 1/00* | (2006.01) | |
| *C08B 1/00* | (2006.01) | |
| *B30B 9/12* | (2006.01) | |
| *C12M 1/26* | (2006.01) | |
| *B30B 9/18* | (2006.01) | |

(52) U.S. Cl.
CPC ... *C08B 1/00* (2013.01); *B30B 9/12* (2013.01); *B30B 9/18* (2013.01); *C12M 21/12* (2013.01); *C12M 33/16* (2013.01); *C12M 45/03* (2013.01)

(58) Field of Classification Search
CPC ............ B01F 15/0251; C08B 37/0036; C08B 37/006; C10J 2300/0916; C10J 2200/158; C10J 2300/0906; C10J 2300/0976; C12M 33/16; C12M 21/04; C12M 21/12; C12P 2201/00; D21C 3/26; D21C 7/00; Y02E 50/16; Y02E 50/10; Y02E 50/343; Y02E 50/15
See application file for complete search history.

(56) References Cited

U.S. PATENT DOCUMENTS

| | | | |
|---|---|---|---|
| 3,941,650 A | | 3/1976 | Schnyder |
| 4,177,105 A | | 12/1979 | Laakso et al. |
| 4,237,226 A | | 12/1980 | Grethlein |
| 4,594,228 A | | 6/1986 | Lambert, Jr. et al. |
| 4,897,155 A | * | 1/1990 | Koteles ............................ 162/18 |
| 5,320,034 A | * | 6/1994 | Eccleston ........................ 100/35 |
| 5,401,361 A | | 3/1995 | Prough et al. |
| 5,547,546 A | | 8/1996 | Prough et al. |
| 5,591,303 A | | 1/1997 | Oulie et al. |
| 5,736,006 A | | 4/1998 | Prough |
| 5,756,098 A | * | 5/1998 | Price et al. .................... 424/770 |
| 5,766,413 A | | 6/1998 | Backlund et al. |

(Continued)

FOREIGN PATENT DOCUMENTS

| | | |
|---|---|---|
| EP | 0670925 B1 | 10/1993 |
| EP | 1203841 A1 | 1/2001 |

(Continued)

OTHER PUBLICATIONS

Pallmann Refiner System PR, The Pallmann Group, 2008.

(Continued)

*Primary Examiner* — David A Rogers
(74) *Attorney, Agent, or Firm* — Armstrong Teasdale LLP (57) ABSTRACT

Methods for producing ethanol from cellulosic biomass and, in particular, methods for controlling steam explosion pretreatment operations are disclosed. In some particular embodiments, the total solids content of biomass entering a pretreatment digester is calculated to provide operational data and feedback control.

28 Claims, 5 Drawing Sheets

(56) References Cited

U.S. PATENT DOCUMENTS

| | | | |
|---|---|---|---|
| 5,968,314 A | 10/1999 | Prough | |
| 5,972,661 A | 10/1999 | Kubera et al. | |
| 5,972,695 A | 10/1999 | Murofushi et al. | |
| 6,109,449 A | 8/2000 | Howk et al. | |
| 6,113,742 A | 9/2000 | Backlund et al. | |
| 6,660,506 B2 | 12/2003 | Nguyen et al. | |
| 6,699,357 B2 | 3/2004 | Snekkenes et al. | |
| 6,843,885 B2 | 1/2005 | Gustavsson et al. | |
| 7,229,524 B2 | 6/2007 | Snekkenes | |
| 2004/0234435 A1 | 11/2004 | Bickham et al. | |
| 2007/0164143 A1* | 7/2007 | Sabourin et al. | 241/261.2 |
| 2007/0227682 A1 | 10/2007 | Lampinen et al. | |
| 2008/0025144 A1 | 1/2008 | Kocienski et al. | |
| 2009/0022570 A1* | 1/2009 | Craig et al. | 414/197 |
| 2009/0221814 A1* | 9/2009 | Pschorn et al. | 536/128 |
| 2009/0308383 A1 | 12/2009 | Shin et al. | |
| 2010/0056774 A1* | 3/2010 | Anand et al. | 536/124 |
| 2010/0317053 A1* | 12/2010 | Stromberg et al. | 435/41 |
| 2011/0079219 A1* | 4/2011 | McDonald et al. | 127/1 |
| 2011/0262984 A1* | 10/2011 | Nguyen | 435/165 |
| 2011/0275860 A1 | 11/2011 | Beldring et al. | |
| 2012/0006320 A1* | 1/2012 | Nguyen | 127/34 |
| 2012/0048974 A1* | 3/2012 | Gitschel | 241/24.13 |
| 2012/0094348 A1* | 4/2012 | Pye et al. | 435/162 |
| 2012/0130065 A1* | 5/2012 | Labeau et al. | 536/98 |
| 2012/0211512 A1 | 8/2012 | Pschorn et al. | |
| 2013/0005010 A1 | 1/2013 | Bell et al. | |
| 2013/0071903 A1* | 3/2013 | Rowland et al. | 435/162 |
| 2013/0143289 A1* | 6/2013 | Van Der Meulen et al. | 435/145 |
| 2014/0175335 A1* | 6/2014 | Anderson et al. | 252/373 |
| 2014/0249237 A1* | 9/2014 | Ferraro et al. | 518/704 |

FOREIGN PATENT DOCUMENTS

| | | |
|---|---|---|
| JP | 59191593 | 10/1984 |
| JP | 2004090049 | 3/2004 |
| JP | 2010253536 | 11/2010 |
| WO | 9409203 | 4/1994 |
| WO | 02090648 A1 | 11/2002 |
| WO | 02099185 A1 | 12/2002 |
| WO | 2008008296 A2 | 1/2008 |
| WO | 2010022511 A1 | 3/2010 |
| WO | 2011007369 A1 | 1/2011 |
| WO | 2011091044 A1 | 7/2011 |
| WO | 2012016180 A2 | 2/2012 |

OTHER PUBLICATIONS

Schell, et al., Dilute-sulfuric Acid Pretreatment of Corn Stover in Pilot-Scale Reactor, Investigation of Yields, Kinetics, and Enzymatic Digestibilities of Solids, Applied Biochemistry and Biotechnology, 2003, pp. 65-85, vol. 105-108, No. 1-3, ISSN: 0273-2289, Humana Press.

Tucker, et al., Effects of Temperature and Moisture on dilute-Acid Steam Explosion Pretreatment of Corn Stover and Cellulase Enzyme Digestibility, Applied Biochemistry and Biotechnology, Biotechnology for Fuels and chemicals, 2003, vol. 105, No. 1-3, ISSN 0273-2289, Humana Press.

Metso, Screw Feeder ADI 260/420/500/600, Mechanical Fiber Screw Feeder, 2009, 2 pages, Metso Paper, Inc.

Noah D. Weiss, et al., Catalyst Impregnation for High Solids Biomass Pretreatment, National Renewal Energy Laboratory, 2008, 24 pages, AIChE Annual Meeting.

International Search Report and Written Opinion, Application No. PCT/US2013/058733, dated Dec. 3, 2013, pp. 10.

Non-Final Office Action, U.S. Appl. No. 13/625,529, dated Apr. 21, 2014, pp. 42.

International Search Report and Written Opinion, Application No. PCT/US2013/058747, dated Jan. 21, 2014, pp. 11.

International Search Report and Written Opinion, Application No. PCT/US2013/058726, dated Jan. 21, 2014, pp. 12.

* cited by examiner

METHODS FOR CONTROLLING PRETREATMENT OF BIOMASS

FIELD OF THE DISCLOSURE

The field of the disclosure relates to methods for producing ethanol from cellulosic biomass and, in particular, methods for controlling steam explosion pretreatment operations. In some embodiments, the total solids content of biomass entering a pretreatment digester is calculated to provide operational data and feedback control.

BACKGROUND

Biofuels such as ethanol have seen increased use as an additive or replacement for petroleum-based fuels such as gasoline. Ethanol may be produced by fermentation of simple sugars produced from sources of starch (e.g., corn starch) or from lignocellulosic biomass.

There are a variety of widely available sources of lignocellulosic biomass including, corn stover, agricultural residues (e.g., straw, corn cobs, etc.), woody materials, energy crops (e.g., sorghum, poplar, etc.), and bagasse (e.g., sugarcane). Lignocellulosic biomass is a relatively inexpensive and readily available feedstock for the preparation of sugars, which may be fermented to produce alcohols such as ethanol.

Preparation of ethanol from biomass involves methods for increasing the accessibility of cellulose to downstream enzymatic hydrolysis. There is a continuing need for methods for producing ethanol from lignocellulosic biomass that provide increased control of the pretreatment process such that consistent and relatively high-yielding pretreated biomass may be produced.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

One aspect of the present disclosure is directed to a method for controlling the total solids contents of biomass discharged from a plug screw feeder into a pretreatment digester. The plug screw feeder includes a throat section having a number of drain openings. The digester is connected to a damper which contacts the biomass material as it enters the digester. The damper is driven forward by a piston which exerts a force on the damper to create a back pressure against the biomass. The flow rate of biomass introduced into the plug screw feeder is measured. The total solids content of biomass introduced into the plug screw feeder is measured. The flow rate of an effluent slurry discharged from the plug screw feeder is measured. The total solids content of the biomass discharged from the plug screw feeder into the pretreatment digester is calculated based on the flow rate and total solids content of biomass introduced into the plug screw feeder and the flow rate of the effluent slurry discharged from the plug screw feeder. At least one of (1) the number of open drain openings in the plug screw feeder throat section, (2) the force exerted on the damper by the piston, (3) the rotational speed of the plug screw feeder and (4) the total solids content of biomass introduced into the plug screw feeder is adjusted based on the calculated total solids content of the biomass discharged from the plug screw feeder.

Another aspect of the present disclosure is directed to a method for producing a pretreated biomass feedstock. A biomass feedstock is contacted with an aqueous acid solution to form an acid-impregnated biomass stream. The acid-impregnated biomass stream is dewatered to produce an effluent slurry and dewatered biomass. A concentration of acid in the effluent slurry is controlled. The dewatered biomass and steam are introduced into a pretreatment digester. A total solids content of dewatered biomass introduced into the pretreatment digester is controlled. The temperature of the pretreatment digester is controlled. An average residence time of biomass in the pretreatment digester is controlled.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
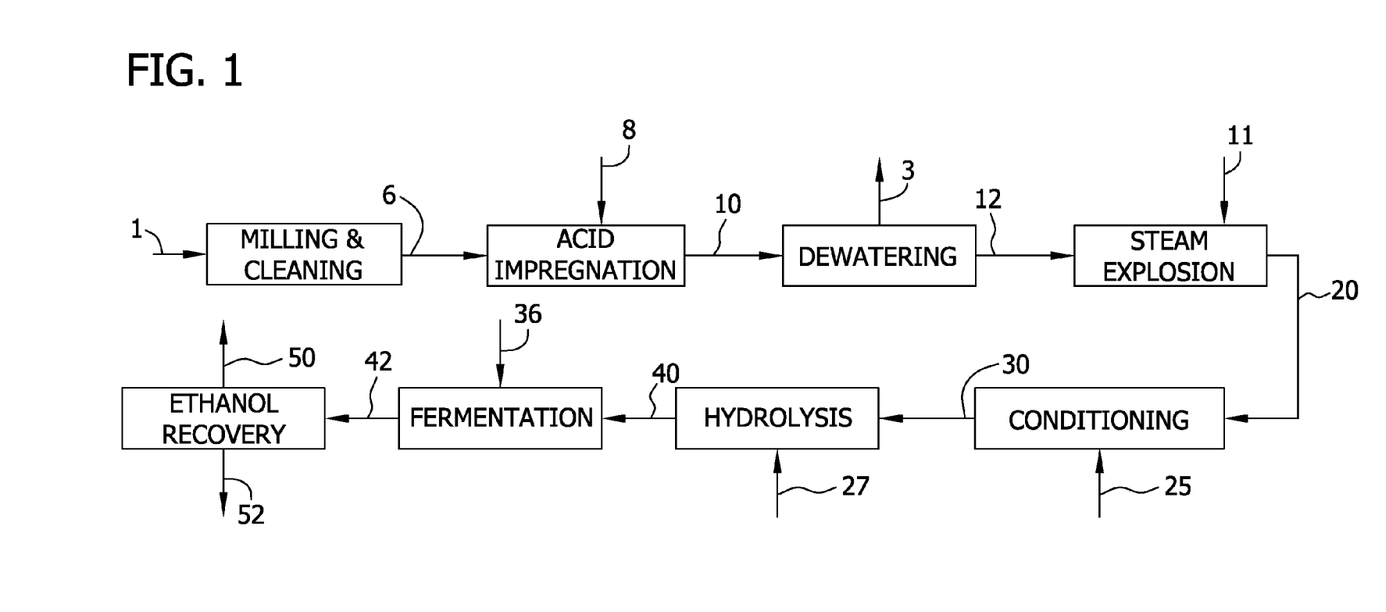
FIG. 1 is a flow chart depicting a method for producing ethanol from a cellulosic biomass feedstock.

In accordance with various embodiments of the present disclosure and with reference to FIG. 1, lignocellulosic biomass material 1 is subjected to milling and cleaning operations to reduce the particle size of the material and to remove any non-biomass contaminants from the feedstock. Any of a variety of biomass materials may be used as the starting feedstock of embodiments of the present disclosure including plant biomass, agricultural or forestry residues, or sugar processing residues. Suitable grass materials include cord grass, reed canary grass, clover, switchgrass, bamboo, marram grass, meadow grass, reed, ryegrass, sugar cane, and grasses from the *Miscanthus* genus. The biomass feedstock may include agricultural residues such as rice straw, rice hulls, barley straw, corn cobs, wheat straw, canola straw, oat straw, oat hulls, corn fiber, stover (e.g., sorghum, soybean stover and/or corn stover) or combinations thereof Sugar processing residues include sugar cane bagasse, sweet sorghum, beet pulp, and combinations thereof The feedstock may also include wood and forestry wastes such as, for example, recycled wood pulp fiber, sawdust, hardwood, softwood, forest thinnings, orchard thinnings, or combinations thereof Other materials such as residential yard waste, wood debris from construction and demolition sites and cellulosic materials sorted from municipal wastes may also be used in the feedstock. The content of such municipal wastes may vary (e.g., from about 15 wt % to about 50 wt % cellulose on a dry basis, from about 5 wt % to about 30 wt % hemicellulose on a dry basis and/or from about 10 wt % to about 40 wt % lignin on a dry basis).

The biomass feedstock may have a cellulose content of at least about 15 wt % on a dry basis or, as in other embodiments, at least about 25 wt %, at least about 30 wt %, at least about 35 wt % or at least about 50 wt % cellulose on a dry basis (e.g., from about 15 wt % to about 55 wt % or from about 25 wt % to about 45 wt %). Alternatively or in addition, the biomass feedstock may contain at least about 5 wt % hemicellulose on a dry basis or at least about 15 wt %, at least about 20% or at least about 25 wt % hemicellulose on a dry basis (e.g., from about 10 wt % to about 30 wt % or from about 15 wt % to about 25 wt %). Alternatively or in addition, the biomass material may include at least about 10 wt % lignin on a dry basis or at least about 15 wt %, at least about 20 wt % or at least about 25 wt % lignin on a dry basis (e.g., from about 10 wt % to about 40 wt % or from about 15 wt % to about 25 wt %). In this regard, the biomass feedstock may contain cellulose, hemicellulose and/or lignin in any range bound by the above-listed parameters and in any combination of respective ranges. The biomass material 1 may be bound by any combination of the above-noted parameters including any combination of the cellulose, hemicellulose and lignin parameters provided above. It should be noted that the recited ranges are exemplary and the biomass feedstock may contain more or less cellulose, hemicellulose and/or lignin without limitation. Any biomass material suitable for preparing fermentable sugars may be used unless stated otherwise.

The feedstock may include components other than cellulose, hemicellulose and lignin such as ash including structural inorganics and may include contaminants (e.g., gravel, sand or dirt). In various embodiments, the biomass feedstock may contain about 1 wt % or less ash on a dry basis, about 3 wt % or less ash, about 5 wt % or less ash or about 8 wt % or less ash on a dry basis. The biomass feedstock may contain moisture and in some embodiments contains at least about 1 wt % (by total weight including moisture) moisture, at least about 5 wt %, at least about 10 wt %, at least about 15 wt % or even at least about 20 wt % moisture (e.g., from about 1 wt % to about 30 wt %, from about 1 wt % to about 20 wt % or from about 5 wt % to about 20 wt % moisture).

The biomass feedstock material may undergo one or more milling operations to reduce the particle size of the material before downstream processing. In some embodiments, the biomass material 1 is reduced to a size less than about 40 mm or from about 2 mm to about 30 mm or from about 5 mm to about 30 mm. Relatively large biomass material (e.g., greater than about 40 mm or greater than about 50 mm) may result in low bulk density which increases the size of equipment (e.g., conveyors) and may impede impregnation and heating. Relatively small biomass (e.g., less than about 2 mm or less than about 0.5 mm) may hold large amounts of liquid resulting in longer heating times. Any equipment suitable to reduce the particle size of the biomass material 1 may be used including, for example, hammermills, grinders, cutters, chippers, crushers and the like. In some embodiments, the biomass feedstock is not milled prior to downstream processing.

Alternatively or in addition, the biomass feedstock may undergo a cleaning operation to remove contaminants from the feedstock. Suitable operations include sifting, air classifying to remove gravel, sand and fines, and contacting the feedstock with one or more magnets to remove ferrous material from the feedstock.

In some embodiments, the milled and cleaned biomass feedstock is preheated with direct steam contact (e.g., less than 1 bar pressure) to open up the pore structure and drive out entrapped air before feeding the biomass to the acid impregnator as described below. The steaming time may be sufficient to heat the biomass to at least about 40° C., at least about 60° C. or at least about 80° C.

After milling, the milled biomass 6 is subjected to an acid impregnation process and steam explosion process to cause the cellulose in the biomass to become more available to enzymatic hydrolysis. Acid impregnation generally involves contacting the milled biomass with acid 8 (e.g., dilute acid) in a vessel for a time sufficient to allow the acid to thoroughly contact and be dispersed throughout the biomass. Any suitable vessel may be used to achieve acid impregnation including pug mixers and stirred tank reactors which may be operated in batch or continuous modes. The biomass may be contacted with acid 8 by spraying and mixing or by soaking and mixing. In embodiments in which spraying and mixing are used to impregnate acid into the biomass, the liquid-to-dry biomass weight ratio may be at least about 2:1, at least about 3:1 or at least about 4:1 (e.g., from about 3:1 to 8:1). In embodiments in which the biomass is soaked and mixed, the liquid-to-dry biomass weight ratio may be at least about 10:1, at least about 12:1 or at least about 14:1 (e.g., from about 12:1 to about 20:1).

The acid 8 that is used for acid impregnation may be sulfuric acid, hydrochloric acid or nitric acid. Regardless of the acid that is used, the concentration of the acid solution added to the biomass may be at least about 0.1 wt %, at least about 0.2 wt %, at least about 0.5 wt %, at least about 1 wt %, at least about 2.5 wt %, less than about 5 wt %, less than about 3 wt %. less than about 2.5 wt %, less than about 1 wt % or less than about 0.5 wt % (e.g., from about 0.2 wt % to about 5 wt % or from about 0.5 wt % to about 3 wt %). The temperature of the acid 8 introduced in the vessel may vary depending on whether the acid-impregnation vessel includes heating elements (resistance heaters, combusted gases, steam or the like) in thermal communication with the vessel or includes direct steam injection for heating the acid and/or milled biomass material 6 during impregnation.

In some embodiments, the acid 8 is heated and/or extraneous heat is applied to the impregnation vessel such that the acid-impregnated biomass 10 is at a temperature of at least about 20° C., at least about 50° C. or at least about 75° C. The amount of time between initial contact of the biomass with acid and before downstream dewatering may be at least about 30 seconds, at least about 1 minute, at least about 5 minutes or more (e.g., from about 30 seconds to about 20 minutes or from about 1 minute to about 10 minutes). The pH of the acid-impregnated biomass 10 may be less than about 5, less than about 3 or less than about 2.

After acid impregnation, the acid-impregnated biomass 10 may undergo a dewatering operation (FIG. 1) to reduce the moisture content of the biomass to an amount suitable for steam explosion.

Suitable equipment for dewatering includes, for example centrifuges, filters and cyclones (e.g., which may also be referred to as "hydro-clones" by those of skill in the art) which may be used for slurries having a total solids content of about 4 wt % of less; screens and drain-screws which may be used for inlet slurries having a total solids content of about 4 wt % to about 18 wt %; and screw presses and plug feeders which may be used for inlet slurries having a total solids content of about 15 wt % to about 40 wt %. Dewatering operations may increase the total solids content of the biomass to about 30 wt % or more, to about 40 wt % or more, to about 50 wt % or more (e.g., from about 30 wt % to about 50 wt % or from about 30 wt % to about 40 wt % total solids). Dewatering produces an effluent slurry 3 (FIG. 1).

After dewatering, the dewatered biomass 12 and steam 11 are introduced into a vessel to cause steam explosion of the biomass material 1. Vessels for causing steam explosion of biomass may be referred to as a "pretreatment digester" or simply "digester" or "pretreatment reactor" or simply "reactor" by those of skill in the art and these terms may be used interchangeably herein. The vessel may have any suitable shape (e.g., cylindrical) and may have a vertical or horizontal orientation. Steam is introduced into the vessel at an elevated pressure. Upon discharge from the vessel, the pressure is reduced rapidly which causes sudden and vigorous flash of liquid (often referred to as steam explosion). The steam explosion causes a change in the structure of the biomass (e.g., a decrease in the particle size and increase in specific surface area of the biomass) which allows the cellulose to be more accessible for downstream enzyme hydrolysis and allows the hemicellulose to be more readily solubilized. The rapid drop in pressure allows a significant portion of the hot condensate to flash off and results in lower temperature and higher solid content of pretreated material.

In some embodiments, the mass ratio of steam 11 to dewatered biomass 12 (based on dry biomass) added to the vessel is at least about 1:6 or, as in other embodiments, at least about 1:4 or at least about 1:1.5. The pressure of steam 11 added to the vessel may be at least about 5 bar, at least about 10 bar or at least about 15 bar. The temperature of steam introduced into the vessel may be from about 150° C. to about 230° C. (e.g., from about 170° C. to about 210° C.).

In some embodiments, the temperature of the biomass material within the vessel is controlled by adjusting the pressure of the process steam 11 added to the vessel. The temperature within the vessel (and of the biomass after sufficient residence time) may be controlled to be from about 160° C. to about 195° C. Temperatures below 160° C. may involve longer residence times resulting in larger digester volumes and even use multiple digesters operating in parallel. Temperatures above about 195° C. may involve relatively low residence times which may result in difficulty in controlling temperature in the digester. The temperature of the vessel may be measured and the pressure adjusted (manually or by automatic control) based on the measured temperature. Non-condensable gases, which could lower the temperature of vapor space inside the digester if allowed to accumulate, may be continuously or intermittently vented from the top section of the digester to prevent build-up. Other methods of controlling the temperature and moisture of the biomass material are contemplated within the scope of this disclosure.

The average residence time of the biomass material within the vessel may also be controlled to produce a more uniform pretreated stream. The average residence time may be controlled, for example, by varying the amount of biomass in the vessel (i.e., adjusting the level of biomass in the vessel for vertical vessels). This average residence time or level may be adjusted by increasing or decreasing the flow rate of material discharged from the vessel (or added to the vessel as in some embodiments) for a period of time until the desired average residence time is achieved.

The level of biomass in the vessel may be measured by any suitable instrument such as a nuclear level measuring instrument. The mass of biomass retained in the vessel may be determined based on estimated (or measured) bulk density and the volume occupied at a particular level. The average residence time may be calculated by dividing the mass biomass retained in the vessel by the average mass flow rate of biomass fed into the digester. Average residence time may also be measured by sending a visible tracer or a tracing chemical through the digester 64. Once the desired average residence time (i.e., level as with vertical vessels) is achieved, the rate of input into the vessel may be returned to a steady-state condition. In embodiments wherein a horizontal digester having a screw conveyor is used, the average residence time may be adjusted by changing the speed of the conveyor. In some embodiments and regardless of whether a vertical or horizontal digester is used, the average residence time may be controlled to be at least about 1 minute (e.g., from about 1 minute to about 30 minutes or from about 1 minute to about 20 minutes). For relatively short residence time (e.g., less than about 1 minute), it may be difficult and less accurate to measure the level of biomass inside the vessel and consequently difficult to precisely control the residence time. Also at low level (i.e., short residence time) there is an increased risk of blowing steam through the short bed of biomass and an uneven discharge of biomass may occur. Upon exiting the vessel, the pressure of the biomass is quickly reduced, which causes the desired structure change in the biomass. This structure change increases the availability of cellulose to undergo downstream hydrolysis. In some embodiments (FIG. 2), the biomass is discharged into a flash vessel 67 that is at a low pressure (e.g., about 0.5 bar to about 3 bar gauge) relative to the digester 64. The pressure difference between the steam vessel and flash vessel may be at least about 5 bar, at least about 9 bar or at least about 12 bar.

Figure 2:
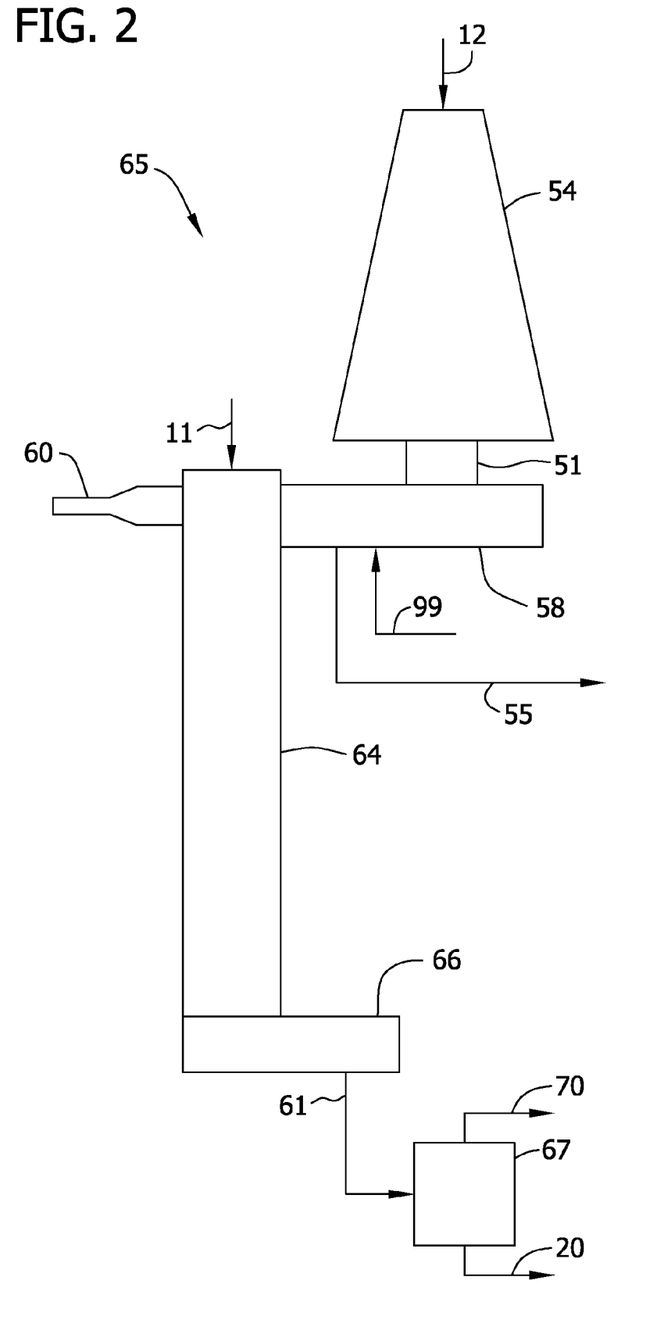
FIG. 2 is a schematic view of a system for pretreating biomass by steam explosion.

Referring now to FIG. 2, a system 65 for causing steam explosion of dewatered biomass material may include a chip silo 54, a pretreatment digester 64 and a plug screw feeder 58 that transfers acid impregnated and dewatered biomass 12 from the silo 54 to the digester 64. The silo 54 is suitably sized to provide sufficient storage capacity to allow acid impregnated and dewatered biomass 12 to be introduced at a relatively constant rate to the pretreatment digester 64. The silo 54 may have a cylindrical shape with a diverging wall (i.e., the diameter of the bottom is larger than the diameter of the top), but may alternatively have another suitable shape.

In accordance with some embodiments of the present disclosure, the system 65 may include a metering device 51 for metering dewatered biomass 12 from the silo 54 to the plug screw feeder 58. Any suitable metering device such as rotary sweepers or agitators may be used. The metering device 51 may operate with a mass weight feeder such as a weight belt metering conveyor (not shown) that feeds dewatered biomass to the silo 54. The mass weight feeder controls the amount of dewatered biomass fed into the silo and the silo metering device 51 maintains the level of biomass in the silo at a constant level. The metering device 51 may enable a relatively steady feed rate (e.g., does not overflow or empty the silo 54) In some embodiments, the moisture content of the dewatered biomass 12 (either entering or at the bottom of the silo 54) may be measured to help determine the total solids content of the biomass discharged into the digester 64 as described below. Measurement of the moisture content of dewatered biomass may be performed using any suitable instrument (e.g., a near infrared spectrophotometer) or by traditional drying method applied to grabbed samples.

Figure 3:
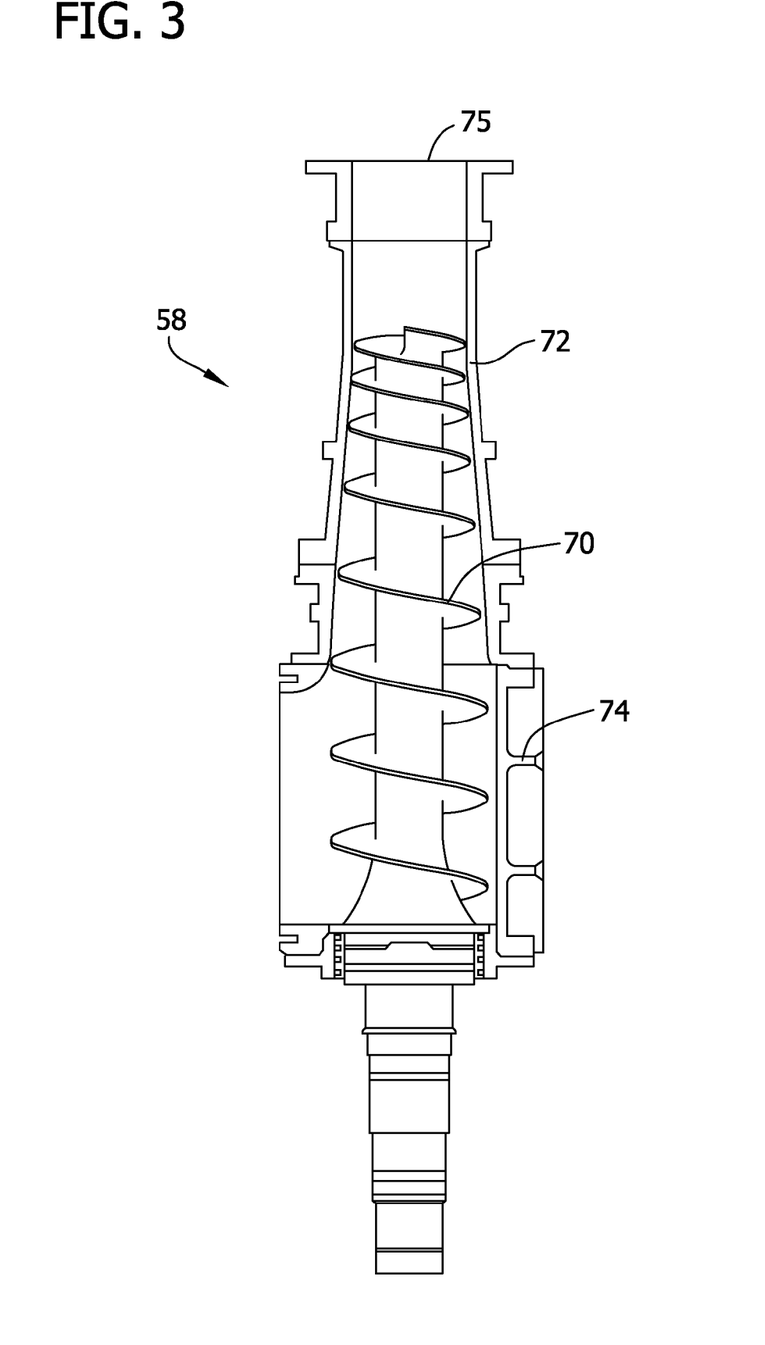
FIG. 3 is a top view of a plug screw feeder with the top portion of the feeder removed.
Figure 4:
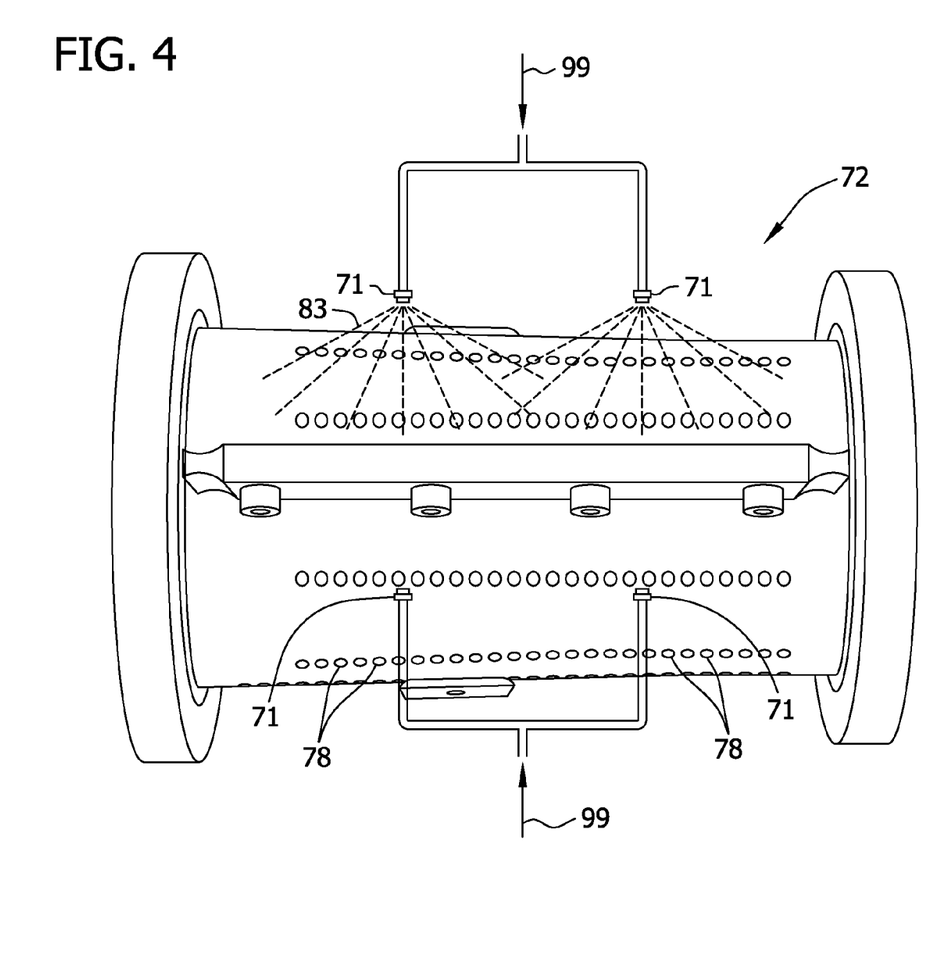
FIG. 4 is a side view of a throat section of a plug screw feeder.

The plug screw feeder 58 (FIG. 3) includes a screw 70 that extends through an inlet housing 74 and throat section 72. The throat section 72 narrows in diameter toward the discharge end 75 of the feeder 58 to compact the biomass as it travels toward the discharge end. The throat section 72 includes a number of openings 78 (FIG. 4) through which liquid passes as the biomass is compressed. The flighting of the screw 70 (FIG. 3) becomes more narrowly spaced toward the discharge end 75 of the plug screw feeder 58. The diameter of the screw flighting also decreases toward the discharge end 75 of the plug screw feeder 58.

As material falls into the plug screw feeder 58 and travels to the discharge end 75 of the plug screw feeder 58, the material compresses and air and effluent slurry 55 (FIG. 2) are forced out of the biomass. The compression generally allows the biomass to achieve a more uniform moisture content that facilitates better downstream control.

Towards the end 75 of the feeder 58 the biomass forms a "plug" which isolates the high pressure digester 64 from the lower pressure (e.g., atmospheric pressure) environment in the inlet of the feeder 58. As more material is pushed forward by the screw 70, the plug of material is pushed forward into the digester 64. As the biomass material enters the digester 64, a blow back damper 80 (FIG. 5) (which may also be referred to herein simply as "damper") contacts the biomass to cause the plug to loosen. Loosening the plug causes the biomass to fall into the digester 64. The damper 80 also exerts force on the biomass which helps form a dense biomass plug to seal against the steam pressure inside the digester or seals the plug screw feeder 58 when a plug of biomass is not present in the feeder.

Figure 5:
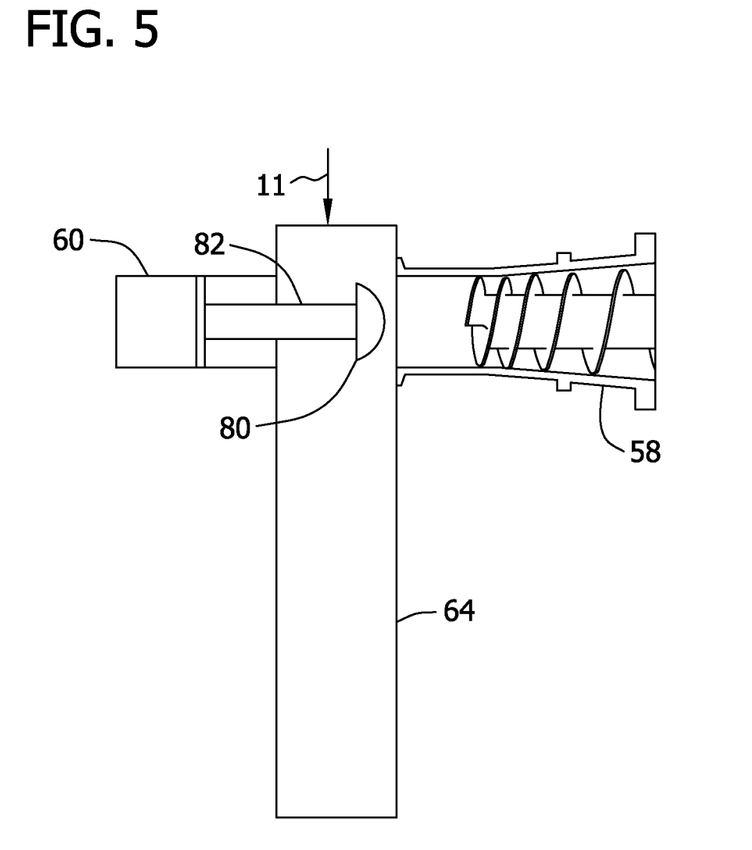
FIG. 5 is a schematic view of a digester, plug feeder and damper assembly.

The damper 80 may form part of a damper assembly 60. The damper assembly 60 may include a piston 82 which exerts a force on the damper 80 to drive the damper forward against the biomass. The piston 82 may be driven forward pneumatically or hydraulically or by any other suitable method. The force applied to the damper 80 may be varied by adjusting the pneumatic or hydraulic pressure applied to the piston 82.

While the pretreatment digester 64 is shown in FIGS. 2 and 5 as being generally vertical, the digester may also be oriented generally horizontally or in other orientations.

Flushing fluid 99 (FIG. 4) may be sprayed on the throat section of the plug screw feeder to prevent buildup of fines expelled through the drain openings 78. The flushing fluid 99 may be process water or acid (e.g., hot dilute acid). At least one spray nozzle 71 is positioned above and to the side of each side of the throat section. For large feeders, two or more spray nozzles 71 may be positioned on each side directing a spray pattern 83 of liquid at the drain openings to prevent buildup of fines and to flush fines down to a collection trough (not shown) positioned below the throat section 72. The spray pattern 83 may be directed at the drain openings 78 in a manner such that the liquid exiting the drain openings is not impeded, i.e., not directly inside the opening but at an angle from above. The rate and pressure of the liquid spray can be adjusted manually or remotely using a flow control valve (not shown) in the flushing fluid supply lines. In some embodiments, the liquid flow rate to each (or selected groups) of spray nozzles may also be adjusted by use of individual flow control valves (not shown). The liquid drainage rates through the openings closer to the entrance of the throat are generally higher than the rates that are nearer to the exit zone; therefore, higher liquid spray rates may be used upstream of the throat to flush away higher amount of fines. The flushing liquid may provide sufficient flow and velocity to carry away fines that may otherwise settle out at the bottom of the trough (not shown) beneath the throat 72 of the plug screw feeder. The flushing liquid may have the same acid concentration and temperature as the dilute acid 8 used for impregnating biomass.

The fluid and fines (which may be biomass and sand) forced through the openings 78 of throat section 72 of the plug screw feeder together with the flushing fluid 99 form an effluent slurry 55 (FIG. 2) that is removed the plug screw feeder 58. In some embodiments, flushing fluid 99 is not used and only fines and liquids discharged from the throat second 72 exit the plug screw feeder (i.e., form the effluent slurry 55).

A mass balance is performed with respect to the plug screw feeder 58 to determine the total solids content of the biomass material which enters the pretreatment digester 64. To determine the total solids content of the material entering the digester 64, the mass flow rate ($FR_{in}$) and total solids content ($TS_{in}$) of material entering the plug screw feeder 58 and the mass flow rate ($FR_{out}$) and total solids content ($TS_{out}$) of the effluent slurry 55 are measured. If flushing fluid 99 is used, the mass flow rate $FR_{FF}$ of the flushing fluid may be measured. The total solids content ($TS_{digest}$) of the material that falls into the digester 64 may be determined as follows:

$$TS_{digest}=(FR_{in}*TS_{in}-FR_{out}*TS_{out})/(FR_{in}+FR_{FF}-FR_{out}) \quad (eq. 1)$$

In embodiments in which no flushing fluid is used, the total solids content ($TS_{digest}$) of the material that falls into the digester 64 may be determined as follows:

$$TS_{digest}=(FR_{in}*TS_{in}-FR_{out}*TS_{out})/(FR_{in}-FR_{out}) \quad (eq. 2)$$

The mass flow rate ($FR_{in}$) of material entering the plug screw feeder 58 (through the hopper 54) may be measured by use of a weight and loss feeder, by a weight belt or by another suitable mass flow meter. Total solids content ($TS_{in}$) of the material entering the plug screw feeder 58 may be determined by sampling the material and measuring the mass of the sample before and after evaporating the moisture by heating (e.g., by infrared (IR) moisture balances). The total solids content may also be measured by near infrared (NIR) moisture analyzers or portable (e.g., handheld) moisture meters.

The mass flow rate ($FR_{out}$) of effluent slurry 55 may be measured by liquid mass flow meters or by collecting the effluent slurry for a period of time and measuring the weight of the collected effluent slurry or measuring the volume of collected liquid and determining the weight using the measure density of the liquid. In some embodiments, the mass flow rate of the effluent slurry 55 is measured by measuring a volumetric flow rate and converting the volumetric flow rate to a mass flow rate based on the measured or approximated density of the effluent slurry.

The total solids content ($TS_{out}$) of the effluent slurry 55 may be determined by gathering a sample and drying the sample in a drying oven or using an IR balance. The total solids content of the effluent slurry 55 may be periodically monitored to detect potential issues with unit operations upstream of the silo 54. High total solids content or increasing amounts of fines in the effluent slurry 55 may indicate that the feedstock milling and cleaning systems may be malfunctioning or that the feedstock may contain excessive amount of fine contaminant (e.g. sand). The solid fines in the slurry effluent 55 may be below about 3 wt %, below about 2 wt % or below about 1 wt % of the total solids entering the silo 54. High fines content in the effluent slurry 55 also may indicate a high amount of fines entering the digester 64 (FIG. 2) which may cause uneven heating of biomass.

In some embodiments, the total solids content of the effluent slurry 55 is assumed to be negligible and is not used to determine the total solids content of biomass material entering the digester. In such embodiments, the total solids content ($TS_{digest}$) of the material that falls into the digester 64 is determined as follows:

$$TS_{digest}=(FR_{in}*TS_{in})/(FR_{in}+FR_{FF}-FR_{out}) \quad (eq. 3).$$

If flushing fluid is not used, the total solids content ($TS_{digest}$) may be determined as follows:

$$TS_{digest}=(FR_{in}*TS_{in})/(FR_{in}+FR_{FF}-FR_{out}) \quad (eq. 4).$$

In some embodiments, the total solids content of the effluent slurry 55 is assumed to be relatively constant and this constant value is used in the calculation of the total solids content of the material entering the digester 64 rather than a directly measured total solids content.

The flow rates and total solids content of the biomass introduced into the plug screw feeder 58 and the effluent slurry discharged therefrom may be directly measured by technicians or laboratory personnel or measurement may be automatically performed on a continuous basis by suitable measurement devices and may be transmitted (e.g., instantaneously) to operators or to automated control processors (e.g., a computer processor). When direct measurement is used, measurement may suitably be performed at predetermined intervals, e.g., on an hourly basis, or longer intervals may be used (e.g., every 4, 8 or 12 hours or daily measurement). Calculation of the total solids content of the biomass entering the pretreatment digester may be performed automatically by the control processor after electronic transmission of the measured parameters to the processor, or alternatively by manual entry of the data into the processor. In lieu of a processor, the calculation can be performed by technicians or laboratory personnel.

After calculation of the total solids content of the dewatered biomass 12 entering the plug screw feeder 58, an adjustment may be made to the dewatering process to change and thereby control the total solids content of the dewatered biomass. In some embodiments, at least one of the following is adjusted after calculation of the total solids content of the biomass entering the pretreatment digester: (1) the number of open drain openings 78 in the plug screw feeder throat section 72 (FIG. 4), (2) the force exerted on the damper 80 by the piston 82 (FIG. 5), (3) the rotational speed of the plug screw feeder or (4) the total solids content of biomass introduced into the plug screw feeder 58.

In some embodiments of the present disclosure, the number of open drain openings 78 in the plug screw feeder throat section 72 (FIG. 4) are controlled, e.g., adjusted to change the total solids content of the dewatered biomass that enters the digester 64 (FIG. 5). Any suitable method may be used to adjust the number of openings. For example, plugs may be inserted or removed from one or more of the openings. Fastened metal bands with multiple plugs that fit in several openings aligned on the same circumferences of the throat may be used to close many openings at the same time. Alternatively or in addition, if biomass material has partially or fully obstructed one or more openings, the biomass material may be removed to allow liquid to drain from the opening. In some embodiments, the throat section 72 of the plug screw feeder 58 is removed and a new throat section with adjusted openings, e.g., more or less openings, or differently sized openings) is installed in response to the calculated total solids content of the biomass entering the digester.

Alternatively or in addition, the force exerted on the damper 80 by the piston 82 (FIG. 5) may be adjusted. For example, by decreasing the force exerted on the damper 80, less resistance is applied to the biomass being discharged from the plug screw feeder 58 which allows for less compaction of biomass and less removal of water through the openings 78 (FIG. 4) of the throat section 72. The force exerted by the piston 82 may be adjusted by, for example, increasing or decreasing the pneumatic or hydraulic pressure used to drive the piston or by decreasing or increasing the piston or damper length. The force exerted on the damper 80 may also be varied using an adjustable tension spring or adjustable weights.

In some embodiments, the total solids content of biomass introduced into the plug feeder 58 is adjusted to change the total solids content of the biomass fed into the digester 64. For example, upstream screw presses (not shown) may be adjusted in a manner similar to the plug screw feeder to cause more or less dewatering of biomass prior to introduction into the plug screw feeder.

In some embodiments, one or more of the above-described adjustment methods are used to achieve a total solids content of biomass introduced into the digester 64 between about 40 wt % to about 60 wt % total solids or, as in other embodiments, from about 45 wt % to about 55 wt % total solids. In this regard, a total solids content below about 45 wt % and in particular below about 40 wt % may cause a high amount of steam condensate to form in the digester 64 which may dilute the acid in the digester, decrease monomeric xylose yield, slow down the heating of biomass and cause uneven heating of biomass due to moisture blocking heating by direct contact of steam. Total solids content above about 55 wt % and, in particular, above about 60 wt % or even about 65 wt % may cause the acid concentration to be increased to obtain the desired mass ratio of acid to solid biomass which may result in formation of undesirable hemicellulose and lignin degradation products. It should be noted, however, that the present disclosure should not be limited to a particular total solids content of biomass introduced into the digester unless stated otherwise.

In some embodiments, a particular total solids set point, $TS_{digest\_set}$, is chosen and adjustments are made such that $TS_{digest\_set}$ does not vary by more than a certain tolerance level (i.e., $TS_{digest\_set} \pm X$). In some embodiments, the tolerance in the total solids content is about ±1 wt % or less, about ±2 wt % or less, about ±5 wt % or less or about ±10 wt % or less.

The total solids content may be controlled as described above or by other suitable methods. The total solids content may be adjusted to at least partially control other digester 64 parameters. For example, the total solids content of the biomass introduced into the digester 64 (i.e., discharged from the plug screw feeder 58) affects the mass ratio of acid to dry biomass introduced into the digester. Accordingly, the mass ratio of acid to dry biomass may be adjusted by adjusting the total solids content of the biomass introduced into the digester 64. The ratio of acid (100% wt basis) to dry biomass ratio may be in the range from 0.005:1 to 0.04:1 or, as in other embodiments, in the range from 0.01:1 to 0.02:1.

The mass ratio of acid to dry biomass introduced into the digester 64 is also affected by the concentration of acid 8 in the acid-impregnated biomass prior to discharge from the plug screw feeder 58. In some embodiments, the concentration (e.g., pH) of the effluent slurry 55 discharged from the plug screw feeder 58 is measured (or the effluent 3 (FIG. 1) discharged from upstream dewatering operations). In line pH or conductivity meters may be used to continually monitor the pH of the effluent slurry 55 or effluent slurry 3. The acid concentration may be adjusted and thereby controlled by increasing or decreasing the concentration of acid in the acid stream 8 that is used as a source of acid during acid impregnation. In some embodiments, the pH of the effluent slurry 3 or effluent slurry 55 is controlled to be between about 1 and about 1.5. The acid concentration may be determined by direct titration with standard caustic solution. In some embodiments, the acid concentration in stream 8 is controlled to be between about 0.1 wt % to about 3 wt % or, as in other embodiments, between about 0.5 wt % to about 2 wt %.

In some embodiments of the present disclosure, a combination of parameters is controlled to provide consistent pretreated biomass 20. For example, (1) the acid concentration of the effluent slurry 55 (FIG. 2) discharged from the plug screw feeder 58 (or the effluent slurry 3 (FIG. 1) discharged in upstream dewatering processes) may be controlled (e.g., to be between about 0.2 wt % and about 1.5 wt %), (2) the total solids content of the biomass discharged from the plug screw feeder (e.g., as calculated) may be controlled (e.g., to be between about 40 wt % to about 60 wt % total solids or from about 45 wt % to about 55 wt % total solids), (3) the average residence time of biomass in the pretreatment digester 64 (FIG. 1) may be controlled (e.g., from about 1 and about 10 minutes), and (4) the temperature in the pretreatment digester may be controlled (e.g., from about 160° C. to about 195° C.).

Biomass may be removed from the bottom of the digester 64 by use of a rotary sweeper (not shown) positioned above a screw conveyor 66 (FIG. 2) which conveys the treated material 61 through a blow valve assembly (not shown) and into a flash vessel 67 in which steam 70 is flashed from the biomass and discharged. After steam explosion of biomass after the blow valve and in the flash vessel 67, the pretreated biomass 20 is subjected to one or more conditioning operations (FIG. 1) which prepare the pretreated biomass for enzyme hydrolysis. Conditioning may involve various mixing operations and adjustment of temperature, pH, total solids content of the pretreated biomass slurry (e.g., addition of alkali solution 25 which may lower the temperature, total solids content, and/or pH of the pretreated biomass). The alkali may react with hydrolysis inhibitors or neutralize such inhibitors.

In some embodiments of the present disclosure, pretreated biomass 20 downstream of the digester 64 and upstream of enzymatic hydrolysis is analyzed to provide feedback information for the pretreatment process. For example, one or more of the following may be determined for feedback control of the pretreatment operations: pH (before conditioning), total solids, liquid fraction composition (e.g., sugars, degradation products of carbohydrates and lignin such as furfural, hydroxymethyl furfural, acetic acid, phenolic compounds), solid fraction composition (e.g., glucan, xylan, lignin (including pseudo-lignin), particle size distribution and color.

In some embodiments, the pH of the steam-exploded biomass before conditioning is controlled to be less than about 2 or even less than about 1.5. Biomass pH of less than about 2 or even less than about 1.5 may result in relatively high solubilization of hemicellulose.

The composition of the water-insoluble fraction of pretreated biomass 20 may be monitored (intermittently or continuously) using any suitable instrument such as a near-infrared (NIR) or Fourier Transform NIR (FT-NIR) spectroscopy with multivariate analysis.

After conditioning, the conditioned feedstock 30 is subjected to one or more hydrolysis operations. In some embodiments of the present disclosure, enzyme 27 (e.g., enzyme dispersed through a liquid medium such as water) is added to the conditioned feedstock to conduct enzymatic hydrolysis of the conditioned feedstock. Suitable enzymes include for example, cellulase, xylanase, β-xylosidase, acetyl esterase, and α-glucuronidase, endo- and exo-glucannase, cellobiase, lignin degrading enzymes and combinations of these enzymes. Enzymatic hydrolysis may be performed in a series of steps and may include a liquefaction step in which the conditioned biomass transitions from a high viscosity slurry to a pumpable low viscosity liquid and a saccharification step in which simple sugars are produced from cellulose and hemicellulose. Enzymatic hydrolysis may involve separation steps in which C5 sugars are separated from cellulose containing streams and/or in which lignin is separated from the biomass. Any suitable method for hydrolysis of hemicellulose and cellulose which results in fermentable (C5 and/or C6 sugars) may be used in accordance with the present disclosure without limitation.

After production of simple sugars, the sugars 40 (C5 and/or C6 sugars) may be fermented to produce ethanol. In this regard, fermentation of C5 and C6 sugars may be conducted together or separately (e.g., sequentially or in parallel in embodiments in which the C5 and C6 sugars are separated). Any suitable yeast 36 may be used depending on the sugar content and type of sugar of the fermentable stream. Saccharification and fermentation may, at least partially, be achieved in the same vessel or these operations may be performed separately.

Fermentation product stream 42 is subjected to various ethanol recovery steps (e.g., distillation and molecular sieving) to recover ethanol 50. A stillage stream 52 may be removed from the distillation bottoms which may be processed to produce various co-products such as dried distillers biomass or dried distillers biomass with solubles.

It should be noted that the process for producing ethanol from biomass feedstock shown in FIG. 1 and as described herein is simplified for clarity and commercial processes may include additional processing steps, equipment, process recycles and the like. Exemplary ethanol production based on biomass feedstock is also described in U.S. Pat. Pub. No. 2012/0006320, which is incorporated herein by reference for all relevant and consistent purposes. It should be further noted that while the processes described herein may be described with reference to dilute acid pretreatment operations (e.g., contacting the biomass with a source of acid containing less than about 5 wt % acid), the processes may also apply to alkali pretreatment and/or auto-hydrolysis pretreatment operations unless stated otherwise.

Compared to traditional methods, the methods described above have several advantages. By controlling one or more pretreatment parameters, a relatively consistent pretreated feedstock with high bioavailability may be obtained. Pretreated biomass with high cellulose digestibility and high solubilization of hemicellulose (e.g., solubilization of xylan in corn stover or deciduous wood) may be consistently produced and degradation of solubilized xylose to furfural or condensation of xylose with lignin to form pseudo-lignin (which may interfere with enzyme accessibility to cellulose) may be minimized. Further, as the total solids content of the biomass entering the digester 64 can not be directly measured, a method for calculating the total solids of the material entering the digester is provided (an indirect measurement or calculation). By controlling the total solids content of biomass entering the digester 64, biomass may be heated relatively uniformly resulting in a more consistent pretreated product.

When introducing elements of the present disclosure or the embodiment(s) thereof, the articles "a", "an", "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing[s] shall be interpreted as illustrative and not in a limiting sense.

What is claimed is:

1. A method for controlling the total solids contents of biomass discharged from a plug screw feeder into a pretreatment digester, the plug screw feeder comprising a throat section having a number of drain openings, the digester being connected to a damper which contacts the biomass material as it enters the digester, the damper being driven forward by a piston which exerts a force on the damper to create a back pressure against the biomass, the method comprising:
- measuring the flow rate of biomass introduced into the plug screw feeder;
- measuring the total solids content of biomass introduced into the plug screw feeder;
- measuring the flow rate of a effluent slurry discharged from the plug screw feeder;
- calculating the total solids content of the biomass discharged from the plug screw feeder into the pretreatment digester based on the flow rate and total solids content of biomass introduced into the plug screw feeder and the flow rate of the effluent slurry discharged from the plug screw feeder; and
- adjusting at least one of (1) the number of open drain openings in the plug screw feeder throat section, (2) the force exerted on the damper by the piston, (3) the rotational speed of the plug screw feeder and (4) the total solids content of biomass introduced into the plug screw feeder based on the calculated total solids content of the biomass discharged from the plug screw feeder.

2. The method as set forth in claim 1 further comprising:
- measuring the total solids content of the effluent slurry discharged from the screw plug feeder; and
- calculating the total solids content of the biomass discharged from the plug screw feeder into the pretreatment digester based on the total solids content of the effluent slurry discharged from the plug screw feeder.

3. The method as set forth in claim 1 wherein a flushing fluid is directed at the drain openings to flush fines from the drain openings, the flushing fluid forming a part of the effluent slurry discharged from the plug screw feeder, the method comprising measuring the flow rate of the flushing fluid.

4. The method as set forth in claim 3 wherein the flushing fluid is directed at the drain openings at an angle with the drain openings to not impede the flow of liquid being discharged from the openings.

5. The method as set forth in claim 4 further comprising adjusting a mass ratio of acid to dry biomass discharged from the plug screw feeder by changing the total solid content of the biomass discharged from the plug screw feeder.

6. The method as set forth in claim 1 comprising contacting a biomass feedstock with an aqueous acid solution to prepare an acid-impregnated biomass stream, the aqueous acid solution having an acid concentration of less than about 5 wt %.

7. The method as set forth in claim 1 comprising introducing biomass discharged from the plug screw feeder and steam into the pretreatment digester.

8. The method as set forth in claim 1 comprising controlling the total solids content of the biomass discharged from the plug screw feeder into the pretreatment digester to be between about 40 wt % to about 60 wt %.

9. The method as set forth in claim 1 comprising controlling the total solids content of the biomass discharged from the plug screw feeder into the pretreatment digester to be between about 45 wt % to about 55 wt %.

10. The method as set forth in claim 1 comprising:
- controlling a concentration of acid in the effluent slurry;
- controlling the temperature of the pretreatment digester; and
- controlling an average residence time of biomass in the pretreatment digester.

11. The method as set forth in claim 1 wherein the flow rate of biomass introduced into the plug screw feeder is a mass flow rate and the flow rate of the effluent slurry discharged from the plug screw feeder is a mass flow rate.

12. The method as set forth in claim 1 wherein the flow rate of effluent slurry discharged from the plug screw feeder is a volumetric flow rate.

13. The method as set forth in claim 1 comprising analyzing biomass downstream from the pretreatment digester and adjusting the total solids content of the biomass discharged from the plug screw feeder into the pretreatment digester based on the analysis.

14. The method as set forth in claim 13 wherein at least one of the pH, total solids content, liquid fraction composition and solid fraction composition of the biomass downstream from the pretreatment digester is analyzed.

15. A method for producing a pretreated biomass feedstock, the method comprising:
- contacting a biomass feedstock with an aqueous acid solution to form an acid-impregnated biomass stream;
- dewatering the acid-impregnated biomass stream to produce a effluent slurry and dewatered biomass;
- controlling a concentration of acid in the effluent slurry;
- introducing the dewatered biomass and steam into a pretreatment digester;
- controlling a total solids content of dewatered biomass introduced into the pretreatment digester;
- controlling the temperature of the pretreatment digester; and
- controlling an average residence time of biomass in the pretreatment digester.

16. The method as set forth in claim 15 wherein the concentration of acid in the effluent slurry is controlled by adjusting a concentration of acid in the aqueous acid solution.

17. The method as set forth in claim 15 wherein the effluent slurry is discharged from a plug screw feeder which feeds biomass to the pretreatment digester.

18. The method as set forth in claim 15 wherein the effluent slurry is discharged from a drain screw or screw press which is used to dewater the biomass.

19. The method as set forth in claim 15 wherein the total solids content of dewatered biomass introduced into the pretreatment digester is controlled by adjusting at least one of (1) the number of open drain openings in a throat section of a plug screw feeder which feeds biomass to the pretreatment digester, (2) the force exerted on a damper which is connected to the digester which contacts the biomass material as it enters the digester, (3) the rotational speed of the plug screw feeder and (4) the total solids content of biomass introduced into a plug screw feeder which feeds biomass to the pretreatment digester.

20. The method as set forth in claim 15 comprising calculating the total solids content of dewatered biomass introduced into the pretreatment digester.

21. The method as set forth in claim 15 wherein the aqueous acid solution has an acid concentration of less than about 5 wt %.

22. The method as set forth in claim 15 wherein the pH of the effluent slurry is controlled to be between about 1 and about 2.

23. The method as set forth in claim 15 wherein the total solids content of the biomass introduced into the pretreatment digester is controlled to be between about 40 wt % to about 60 wt %.

24. The method as set forth in claim 15 wherein the total solids content of the biomass introduced into the pretreatment digester is controlled to be between about 45 wt % to about 55 wt %.

25. The method as set forth in claim 15 wherein the temperature of the pretreatment digester is controlled to be from about 160° C. to about 195° C.

26. The method as set forth in claim 15 wherein the average residence time of biomass in the pretreatment digester is controlled to be at least about 1 minute.

27. The method as set forth in claim 15 comprising analyzing biomass downstream from the pretreatment digester and adjusting at least one of (1) the concentration of acid in the effluent slurry, the (2) total solids content of dewatered biomass introduced into the pretreatment digester, (3) the temperature of the pretreatment digester and (4) the average residence time of biomass in the pretreatment digester based on the analysis.

28. The method as set forth in claim 27 wherein at least one of the pH, total solids content, liquid fraction composition and solid fraction composition of the biomass downstream from the pretreatment digester is analyzed.

* * * * *